United States Patent [19]

Sitte et al.

[11] Patent Number: 4,484,503
[45] Date of Patent: Nov. 27, 1984

[54] MICROTOME HAVING A FORWARD-FEED CONTROL SYSTEM FOR THE SPECIMEN ARM AND/OR THE KNIFE

[75] Inventors: Helmuth Sitte, Seefeld; Walter Bilek, Vienna, both of Austria

[73] Assignee: C. Reichert Optische Werke AG, Vienna, Austria

[21] Appl. No.: 513,550

[22] Filed: Jul. 14, 1983

[51] Int. Cl.³ .............................................. G01N 1/06
[52] U.S. Cl. ...................................... 83/717; 83/412; 83/563; 83/915.5
[58] Field of Search ...................... 83/915.5, 717, 718, 83/412, 563

[56] References Cited

U.S. PATENT DOCUMENTS

| | | | |
|---|---|---|---|
| 3,496,819 | 2/1970 | Blum | 83/915.5 X |
| 3,845,659 | 11/1974 | Wikefeldt et al. | 83/915.5 X |
| 4,331,054 | 5/1982 | Williams et al. | 83/915.5 X |

*Primary Examiner*—Frank T. Yost
*Attorney, Agent, or Firm*—Alan H. Spencer; Stephen Raines

[57] ABSTRACT

A microtome, especially an ultramicrotome, is disclosed in which a forward-feed system for the specimen arm and/or knife of the microtome comprises a stepping motor which is controlled by a pulse generator and which shifts the specimen arm, and the knife, relative to each other by an appropriate amount of forward feed in accordance with a forward-feed value which is set at one of a plurality of preselector switches. In order to facilitate quick switching over from one forward-feed amplitude to another, permitting the selection of forward-feed amplitudes which differ by an order of magnitude, for example, if semi-thin sections are to be produced during a run of ultra-thin sections, the forward-feed amplitudes set by the preselector switches can be switched, according to choice, to the pulse generator for the stepping motor by means of a changeover switch. This arrangement enables the operator to alter the forward-feed amplitude by one manual action without disturbing the ongoing operation.

7 Claims, 2 Drawing Figures

MICROTOME HAVING A FORWARD-FEED CONTROL SYSTEM FOR THE SPECIMEN ARM AND/OR THE KNIFE

BACKGROUND OF THE INVENTION

The invention relates to a microtome having a forward-feed control system for the specimen arm and/or the knife, and is especially applicable to an ultramicrotome.

In order to set the section thickness of the thin sections which are produced by means of a microtome, the specimen arm, carrying the preparation or specimen, is shifted towards the knife, before each cutting stroke, by an amount corresponding to the section thickness. In a known ultramicrotome, this is effected by means of a forward-feed mechanism. It is desirable to be able to set an ultramicrotome to produce section thicknesses which differ by several orders of magnitude so that, for example, when starting to cut up a preparation block, considerably thicker sections can initially be removed until a sectioning area, which can be used for a thin section proper, has itself been obtained on the preparation. In a known ultramicrotome, two preselector switches are provided for this purpose, the switches permitting substantially different section thicknesses to be set by the setting of forward-feed values. In an arrangement of this type, the forward-feed value desired for ultra-thin sectioning is set at one of the preselector switches while the forward-feed value desired during the initial cutting process is set at the other preselector switch. When the sectioning surface which produces the first usable thin section is reached on the preparation, the preselector switch, which defines the forward-feed amplitude during the initial cutting process, is turned to the stop position so that the ultramicrotome now operates with the forward feed which corresponds to the desired ultra-thin section thickness.

During the production of ultra-thin sections, it is frequently desired to produce a number of semi-thin sections, or it is necessary to "leap-frog" unusable parts of the preparation, for which purpose the forward feed is increased. In the case of the known ultramicrotome, this requires that the first preselector switch be reset. This proves to be troublesome, particularly during the deliberate inclusion of a few semi-thin sections, not only because resetting involves a delay, but also because the operator is distracted from the operations taking place on the preparation so that it is difficult to exclude the possibility of mistakes.

OBJECT OF THE INVENTION

The object of the invention is accordingly to provide a forward-feed control system, of the type initially mentioned, which permits different forward-feed amplitudes to be selected quickly, without hindering the ongoing work, and without involving any substantial disturbance in the ease with which the cutting process can be observed.

BRIEF DESCRIPTION OF THE INVENTION

According to one aspect of the invention, there is provided a microtome comprising a specimen arm for holding a specimen to be sectioned, a knife for cutting sections from said specimen, a drive means for reciprocating the specimen arm so that said arm moves in a cutting stroke past the knife and in a return stroke, and forward-feed means for incrementally advancing the specimen arm towards the knife before each cutting stroke, the forward-feed means comprising a stepping motor, drive-translation means for translating the motion produced by the stepping motor into linear motion of the specimen arm, a pulse generator connected to the stepping motor to supply voltage pulses to operate said motor, electrical-circuit means adapted to provide two or more alternate outputs, and selector means connected between the electrical-circuit means and the pulse generator for connecting a selected one of the outputs to the pulse generator whereby the specimen arm may be advanced by a selected one of two or more different increments before each cutting stroke.

In another aspect of the invention, the forward-feed means advances the knife instead of, or additionally to, the specimen arm.

The desired different forward-feed values can be set, and remain set, at the various preselector switches, these values normally differing by orders of magnitude. If, for example, it is intended to "fit in" a number of semi-thin sections during the production of ultra-thin sections, the operator needs only to have set the desired forward-feed amplitude at the appropriate preselector switch, after which he can change over, from the ultra-thin section thickness to the semi-thin section thickness, by means of a single manual action at the changeover switch. There is no need to search again for the desired section thickness, nor to set it at the preselector switch.

Digital-type presetting switches are expediently provided as the preselector switches. In one embodiment of the invention, there are provided two stepping motors, of which one is connected to the specimen arm and the other is connected to the knife holder, a preselector switch being assigned to each stepping motor.

BRIEF DESCRIPTION OF THE DRAWINGS

Further advantages and features of the invention are evident from the following description of an illustrative embodiment, with reference to the drawings, in which.

DETAILED DESCRIPTION OF THE INVENTION

Figure 1:
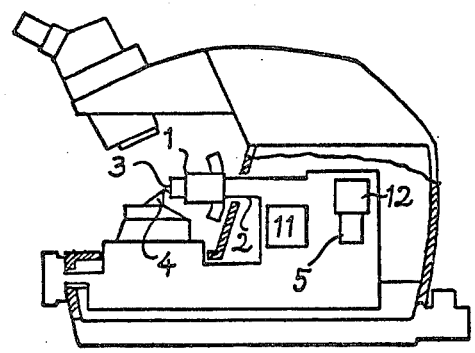
FIG. 1 shows a purely diagrammatic side view of an ultramicrotome, partially sectioned.

The ultramicrotome represented in FIG. 1 includes a specimen carrier 1, which is fastened to a specimen arm 2 and which holds at its front end a specimen or preparation 3. A drive device, which is not shown in more detail, guides the specimen arm 2, and hence the specimen carrier 1 with the preparation, past a knife 4. In addition, a forward-feed device, which is also not shown in detail, shifts the specimen arm 2 towards the knife 4 by a preselectable forward-feed amplitude so that thin sections of a predeterminable thickness can be produced at each cutting stroke. In the design of the devices for driving the specimen arm, and its mode of operation, the ultramicrotome does not differ from known ultramicrotomes, and will, therefore, not be described in more detail.

Figure 2:
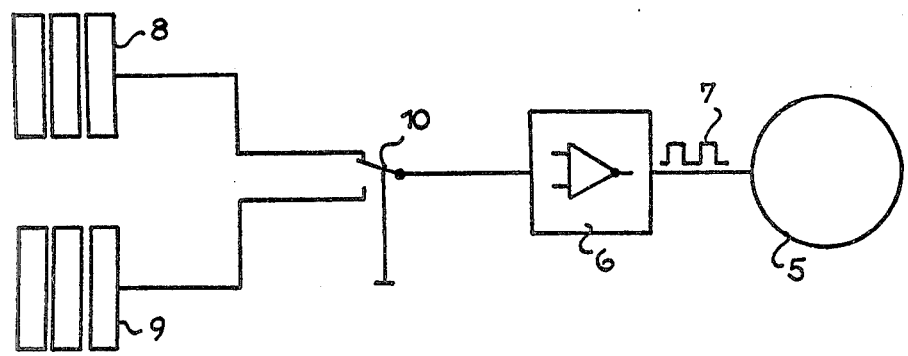
FIG. 2 shows a forward-feed control system, employed in the ultramicrotome shown in FIG. 1.

The control system for the forward-feed device, represented schematically in FIG. 2, makes it possible to control the amplitude of the forward-feed travel executed by the specimen arm 2. For this purpose, the specimen arm 2 is coupled to a stepping motor 5, through a drive translation arrangement which is not shown in detail. The stepping motor 5 receives a pulsed voltage 7 which is supplied via a power-output state 6 incorporating a pulse generator. The specimen arm 2 is moved onwards by a defined number of steps corresponding to the number of pulses. The total number of steps corresponds, in each case, to the forward-feed amplitude at the specimen arm 2.

Digital-type presetting switches 8, 9 are provided for the purpose of presetting forward-feed values of different amplitudes, these presetting switches being capable of being connected, in alternation, to the power-output stage 6. Connection is effected via a changeover switch 10. The desired ultra-thin section thickness is, for example, set at a preselector switch 8, and a semi-thin section thickness is set at the preselector switch 9, the latter being intended to be brought into action during the operation. By simply resetting the changeover switch 10, the operator of the ultramicrotome can consequently set a forward-feed amplitude, at the stepping motor 5, which differs by an order of magnitude, for example, by a power of 10.

One embodiment of the invention provides a plurality of preselector switches, of the above-mentioned type, for a plurality of forward-feed amplitude ranges, in place of the two digital-type preselector switches 8, 9 which are shown in the illustrative embodiment, thus enabling, for example, an even larger section thickness to be selected for the initial cutting operation.

We claim:

1. A microtome comprising a specimen arm for holding a specimen to be sectioned, a knife for cutting sections from said specimen, a drive means for reciprocating the specimen arm so that said arm moves in a cutting stroke past the knife and in a return stroke, and forward-feed means for incrementally advancing the specimen arm towards the knife before each cutting stroke, the forward-feed means comprising a stepping motor, drive translation means for translating the motion produced by the stepping motor into linear motion of the specimen arm, a pulse generator connected to the stepping motor to supply voltage pulses to operate said motor, electrical circuit means adapted to provide two or more alternate outputs, and selector means connected between the electrical circuit means and the pulse generator for connecting a selected one of the outputs to the pulse generator, whereby the specimen arm may be advanced by a selected one of two or more different increments before each cutting stroke.

2. A microtome according to claim 1 wherein the electrical circuit means comprises a respective preselector switch associated with each of said outputs, whereby the output may be adjusted.

3. A microtome according to claim 2 wherein the preselector switches are digital presetting switches.

4. A microtome comprising a specimen arm for holding a specimen to be sectioned, a knife for cutting sections from said specimen, a drive means for reciprocating the specimen arm so that said arm moves in a cutting stroke past the knife and in a return stroke, and forward-feed means for incrementally advancing the knife towards the specimen arm before each cutting stroke, the forward-feed means comprising a stepping motor, drive translation means for translating the motion produced by the stepping motor into linear motion of the knife, a pulse generator connected to the stepping motor to supply voltage pulses to operate said motor, electrical circuit means adapted to provide two or more alternate outputs, and selector means connected between the electrical circuit means and the pulse generator for connecting a selected one of the outputs to the pulse generator, whereby the knife may be advanced by a selected one of two or more different increments before each cutting stroke.

5. A microtome according to claim 4 wherein the electrical circuit means comprises a respective preselector switch associated with each of said outputs, whereby the output may be adjusted.

6. A microtome according to claim 5 wherein the preselector switches are digital presetting switches.

7. A microtome comprising a specimen arm for holding a specimen to be sectioned, a knife for cutting sections from said specimen, a drive means for reciprocating the specimen arm so that said arm moves in a cutting stroke past the knife and in a return stroke, first forward-feed means for incrementally advancing the specimen arm towards the knife, second forward-feed means for incrementally advancing the knife towards the specimen arm, each forward-feed means comprising electric motor means and electrical circuit means controlling the operation of the motor means, the two electrical circuit means being arranged such that the first forward-feed means advances the specimen arm by a different increment to that by which the second forward-feed means advances the knife, and selector means connected between the electrical circuit means and the electric motor means for selectively operating one of the two forward-feed means.

* * * * *